United States Patent [19]
Delespaul et al.

[11] Patent Number: 5,520,936
[45] Date of Patent: May 28, 1996

[54] FOOD ADDITIVE INTENDED FOR HUMAN CONSUMPTION AND AS ANIMAL FEED AND FOODSTUFFS CONTAINING IT

[75] Inventors: Gilbert Delespaul; Philippe Dhoms, both of Vendome; Pierre Raibaud, Jouy-en-Josas; Odette Szylit, Igny, all of France

[73] Assignee: Fromageries Bel, Paris, France

[21] Appl. No.: 157,049

[22] PCT Filed: Jun. 2, 1992

[86] PCT No.: PCT/FR92/00484

§ 371 Date: Jan. 31, 1994

§ 102(e) Date: Jan. 31, 1994

[87] PCT Pub. No.: WO92/21246

PCT Pub. Date: Dec. 10, 1992

[30] Foreign Application Priority Data

Jun. 3, 1991 [FR] France .................... 91 06641

[51] Int. Cl.⁶ ............... A23C 9/12; A01N 63/00; C12N 9/24; A01J 11/00
[52] U.S. Cl. ............... 426/61; 424/93.1; 424/93.2; 424/93.3; 424/93.45; 424/93.46; 99/452; 435/200; 435/252.1; 435/252.9
[58] Field of Search ............... 99/452; 424/93 D, 424/93 J, 93.1, 93.2, 93.3, 93.45, 93.46; 435/200, 252.1, 252.9; 426/61

[56] References Cited

U.S. PATENT DOCUMENTS 3,262,862  7/1966  Kitahara .

FOREIGN PATENT DOCUMENTS 122104  10/1984  European Pat. Off. .
190770  8/1986  European Pat. Off. .

OTHER PUBLICATIONS

Botha et al. "Resistance of Sporolactobacillus . . . ", Int. J. Food Microbiol. 5(4) p. 331–336 (1987).

T. Masaki et al., "Continuous Production of D–Lactate by a Hollow Fiber Bioreactor", *Chemical Abstracts*, vol. 111, No. 17, Oct. 23, 1989, Abstract No. 152007F, p. 565.

R. Gherna et al., American Type Culture Collection, Catalogue of Bacteria and Phages, Seventeenth Edition, 1989, col. 2, lines 42–47, p. 201.

T. Karki et al., "Microorganisms Associated with Various Pickles", *Biological Abstracts*, vol. 79, No. 3, 1985, p. AB–326.

S. Doores et al., "Heat Resistance of *Sporolactobacillus inulinus*", *Journal of Food Science*, vol. 46, No. 3, 1981, pp. 810–812.

*Primary Examiner*—Charles L. Patterson, Jr.
*Assistant Examiner*—Hyosuk Kim
*Attorney, Agent, or Firm*—Bell, Seltzer, Park & Gibson

[57] ABSTRACT

A microbial food additive for human consumption or as animal feed comprises at least one isolated strain of Sporolactobacillus selected from the group consisting of *Sporolactobacillus inulinus* and Sporolactobacillus P44. An isolated strain of Sporolactobacillus having Collection Nationale de Culture de Microorganisms of Institute Pasteur Deposit No. I-1089 is described. Supplemented foodstuffs, both animal feed and for human consumption, contain these microbial food additives.

6 Claims, 1 Drawing Sheet

| | CODE | | | | | | |
|---|---|---|---|---|---|---|---|
| CONTROL | | | | | | | 0 |
| GLYCEROL | | | | | | | 1 |
| ERYTHRITOL | | | | | | | 2 |
| D. ARABINOSE | | | | | | | 3 |
| L. ARABINOSE | | | | | | | 4 |
| RIBOSE | | | | | | | 5 |
| D. XYLOSE | | | | | | | 6 |
| L. XYLOSE | | | | | | | 7 |
| ADONITOL | | | | | | | 8 |
| β METHYL-XYLOSIDE | | | | | | | 9 |
| GALACTOSE | | | | | | | 10 |
| D. GLUCOSE | | | | | ■ | ■ | 11 |
| D. FRUCTOSE | | | | | ■ | | 12 |
| D. MANNOSE | | | | | ■ | | 13 |
| L. SORBOSE | | | | | | | 14 |
| RHAMNOSE | | | | | | | 15 |
| DULCITOL | | | | | | | 16 |
| INOSITOL | | | | | | | 17 |
| MANNITOL | | | | ■ | | | 18 |
| SORBITOL | | | | | | | 19 |
| α METHYL D. MANNOSIDE | | | | | | | 20 |
| α METHYL D. GLUCOSIDE | | | | | ■ | | 21 |
| N. ACETYL GLUCOSAMINE | | | | | ■ | | 22 |
| AMYGDALINE | | | | | | | 23 |
| ARBUTINE | | | | | | | 24 |
| ESCULINE | | | | | | | 25 |
| SALICINE | | | | | | | 26 |
| CELLOBIOSE | | | | | | | 27 |
| MALTOSE | | | | ■ | | | 28 |
| LACTOSE | | | | | | | 29 |
| MELIBIOSE | | | | | | | 30 |
| SACCHAROSE | | | | | ■ | ■ | 31 |
| TREHALOSE | | | | | ■ | | 32 |
| INULINE | | | | | | | 33 |
| MELEZITOSE | | | | | | | 34 |
| D. RAFFINOSE | | | | | ■ | | 35 |
| STARCH | | | | | | | 36 |
| GLYCOGEN | | | | | | | 37 |
| XYLITOL | | | | | | | 38 |
| β GENTIOBIOSE | | | | | | | 39 |
| D. TURANOSE | | | | | ■ | | 40 |
| D. LYXOSE | | | | | | | 41 |
| D. TAGALOSE | | | | | ■ | | 42 |
| D. FUCOSE | | | | | | | 43 |
| L. FUCOSE | | | | | | | 44 |
| D. ARABITOL | | | | | | | 45 |
| L. ARABITOL | | | | | | | 46 |
| GLUCONATE | | | | ■ | | | 47 |
| 2 KETO-GLUCONATE | | | | | | | 48 |
| 5 KETO-GLUCONATE | | | | | | | 49 |

FOOD ADDITIVE INTENDED FOR HUMAN CONSUMPTION AND AS ANIMAL FEED AND FOODSTUFFS CONTAINING IT

FIELD OF THE INVENTION

The present invention relates to a new microbial food additive, to its application as bioregulator both in food for human consumption and in animal feed as well as to foodstuffs containing it.

BACKGROUND OF THE INVENTION

Generally, for the purposes of the present invention, a bioregulator is a product which contributes to the digestive and microbial balance of the intestine. The latter is essentially of microbial origin and there may be mentioned among the most widely known for which this bioregulatory activity has been demonstrated:

Gram+ bacteria such as Lactobacillus, Streptococcus, Propionibacterium, Bifidobacterium, some Clostridium and Bacillus;

Gram— bacteria such as Bacteroides;

yeasts: Saccharomyces;

fungi, such as Aspergillus.

They are used, according to the foodstuffs into which they are incorporated and according to the desired effect, alone or in combination, and in this latter case, in particular for their symbiotic effect.

There may be mentioned, by way of examples of bioregulators used in food for human consumption, the microorganisms used in fermented milks, mainly the bacteria in yogurt or similar products (combination of *Lactobacillus bulgaricus, Streptococcus thermophilus, Lactobacillus acidophilus*, Bifidobacteria, and the like), or kefir grains (natural combination of bacteria and yeasts); there may be mentioned by way of examples of bioregulators used in animal feed, some Bacillus such as *Bacillus toyoi, Bacillus cereus* or a symbiotic mixture of Streptococcus and Lactobacillus as described in European Patent Application No. 0,406,117.

SUMMARY OF THE INVENTION

A first aspect of the present invention is an isolated strain of Sporolactobacillus having Collection Nationale de Culture de Microorganisms of Institute Pasteur Deposit No. I-1089.

A second aspect of the present invention is a microbial food additive for human consumption or as animal feed, which contains an isolated strain of either *Sporolactobacillus inulinus* or Sporolactobacillus P44.

A third aspect of the present invention is a microbial food additive consisting of the Sporolactobacillus P44 strain having Collection Nationale de Culture de Microorganisms of Institute Pasteur Deposit No. I-1089.

A further aspect of the present invention is a microbial food additive consisting of an association of Sporolactobacillus P44 and *Sporolactobacillus inulinus*, acting in symbiosis.

A further aspect of the present invention is supplemented foodstuffs for use as animal feed or for human consumption, which foodstuffs contain a microbial food additives containing an isolated strain of either *Sporolactobacillus inulinus* or Sporolactobacillus P44.

BRIEF DESCRIPTION OF THE DRAWING

FIG. 1 is a profile for the fermentation of sugars by the Sporolactobacillus P44 strain.

DETAILED DESCRIPTION OF THE INVENTION

Numerous hypotheses and mechanisms have been proposed to explain the bioregulatory role of these microorganisms; among the mechanisms proposed, there may be mentioned in particular:

antimicrobial activity: these microorganisms are reported to prevent the proliferation of pathogenic bacteria by producing organic acids, antibiotics, by detoxifying bacterial enterotoxins or by using the production of toxic metabolites. However, the precise role of each of these factors is difficult to evaluate because many studies performed in vitro are difficult to transpose to the human or animal intestinal tract and currently no human experimentation makes it possible to assert an antimicrobial effect in vivo, stimulation of the immune system: it was observed that the regular absorption of yogurts and consequently of the strains present in yogurt (*Lactobacillus bulgaricus, Streptococcus thermophilus*) by axenic mice resulted in a substantial increase in the quantity of immunoglobulin G and in the presence of live Lactobacillus in the mesenteric ganglia, enhancement of the digestive capacity of the small intestine, an enzymatic induction which may have two origins:

the β-galactosidase of the bioregulators is thought to hydrolyse a portion of the lactose ingested in the small intestine, thus resulting in supplementation of the defective endogenous lactose, the bioregulators ingested per os are thought to stimulate the endogenous lactase. It has been shown that a change in the intestinal microflora might be responsible for the disaccharide activities of the small intestine.

Indeed, in order to be assimilated, the lactose present in the intestinal lumen should be hydrolysed by a glycoprotein situated at the surface of enterocytes, known as lactase. This hydrolysis is essential for the assimilation of lactose, the latter being capable of being reabsorbed in the intestine only in its glucose and galactose forms.

However, a large portion of the population is deficient in this enzyme, either for genetic reasons or because its activity decreases with age, thus preventing these populations from consuming any lactose-rich products.

Now, it has been shown that yogurt, although containing a large quantity of lactose can be assimilated by persons having a lactase deficiency, which suggests that the microorganisms present in yogurt permit the assimilation of lactose.

Milk being a basic food for mammals (man and breeding mammals), it is necessary to ensure good assimilation of lactose, which is an important constituent of milk and of certain dairy products, and this throughout their lifetime; in this regard, the microbial bioregulators, exemplified by those present in fermented milks can, by their β-galactosidase activity, be precious aids in this assimilation.

However, in the case of the milk products of the prior art which contain microbial bioregulators, these products have a short shelf life, even at low temperature, because of the impossibility of stabilizing them by thermal treatments, because such treatments could destroy the usual bioregulators present in the digestive tract and which have a β-galactosidase activity, and could thus render these products ineffective in the digestive tract.

Accordingly, the aim of the Applicant was to provide a microbial food additive comprising a strain of Sporolactobacillus, which is particularly useful as bioregulator of lactose, and which is more suitable for the requirements of practical use than the additives of the prior art, especially in that they are provided in the form of natural spores which are resistant to thermal treatments, and more particularly to pasteurization, which is customarily used in processes for the manufacture of milk products, or to steam granulation, which is used in the preparation of pelletized feeds for use as animal feed, and in that it thus increases the shelf life of foodstuffs containing it.

The subject of the present invention is a strain of Sporolactobacillus, characterized in that the DNA of the said bacterium has especially sites of cleavage by the restriction endonucleases BglII, ClaI, SmaI, XbaI, BglI, PvuII, EcoRI, HindIII, EcoRV, XhoI, PstI, MluI, the said restriction enzymes providing the following fragments respectively (expressed in kilobase pairs in Kbp):

BglII: 20.4 - 14.9 - 8.7 - 7.2.
ClaI: 9.5 - 9.3 - 7.6 - 6.8 - 6.4 - 4.2 - 3.2 - 2.6.
SmaI: 20.4 - (16.7) - (14.9) - 13.5 - 10.5 - (8.3) - 7.6 - 5.9 - 4.0.
XbaI: 20.4 - 19.8 - 18.5 - 10.5 - 8.3 - 6.8 - (4.5) - (2.0).
BglI: (20.4) - 18.5 - (16.7) - 12.6 - 10.7 - 6.8.
PvuII: 14.9 - 12.5 - 10.6 - 8.4 - 7.5 - 6.5 - (3.2).
EcoRI: 14.4 - 10.6 - 5.8 - 5.3 - 3.5 - 2.7 - 2.5.
HindIII: 17.0 - 7.9 - 7.4 - 7.0 - 5.3 - 3.8 - 3.7 - 3.5 - (3.3) - (3.2) - (2.9) - 1.8.
EcoRV: (17.0) - 13.2 - 12.0 - 8.1 - 6.3 - 5.3 - (3.5).
XhoI: 22.8 - 20.6 - 8.5 - 8.1.
PstI: 13.2 - 8.5 - 7.8 - 7.3 - 7.0 - 6.6 - (4.1) - (3.2) - (2.5).
MluI: (20.6) - 17.0 - 9.5 - 8.1 - 7.0 - 5.8.

Sporolactobacillus genus has been more particularly described in BERGEY's Bacteriological Manual (Ed. Lavoisier, 1986, 1139–1141).

The method of enzymatic cleavage is that described by GRIMONT (Annales de l'Institut Pasteur Microbiologie, 1986, 137B, 165–175).

This new strain, termed by the inventors, Sporolactobacillus P44, has been deposited with the Collection Nationale de Culture de Microorganismes of INSTITUT PASTEUR, on 30 Apr. 1991, under No. I-1089.

This Sporolactobacillus strain exhibits especially properties of bioregulators of lactose assimilation not by its β-galactosidase activity but by an endogenous intestinal lactase-inducing effect.

The subject of the present invention is also a microbial food additive for human consumption or as animal feed, characterized in that it comprises at least one strain of Sporolactobacillus which exhibits bioregulatory properties, especially with respect to the assimilation of lactose.

According to an advantageous embodiment of the said microbial food additive, the Sporolactobacillus strain is selected from species belonging to the taxonomic genus Sporolactobacillus and especially *Sporolactobacillus inulinus* and Sporolactobacillus P44, as described above.

The species *Sporolactobacillus inulinus*, of which the reference strain is deposited under the No. ATCC/15538, is more particularly described in BERGEY's Bacteriological Manual (Ed. Lavoisier, 1986, p. 1139–1141).

Such an additive has a number of advantages, especially linked to the presence of at least one strain of Sporolactobacillus; indeed, unexpectedly, the additive conforming to the invention:

withstands thermal treatments, more particularly pasteurization and steam granulation, especially because of the possibility of existing in the form of natural spores; and has, both in the form of foodstuffs and additives intended for human consumption and as animal feed, bioregulatory properties for the assimilation of lactose by an endogenous lactose-inducing effect.

According to another advantageous embodiment of the additive conforming to the invention, it comprises at least the Sporolactobacillus P44 strain conforming to the invention.

According to yet another advantageous embodiment of the additive conforming to the invention, it comprises, in addition, in combination any other appropriate strain which acts in symbiosis or as a complement of the Sporolactobacillus strain(s).

Such an additive advantageously comprises the combination of two strains belonging to the Sporolactobacillus genus.

In conformity with the invention, the additive can, in addition, be also combined with carriers, diluents, preservatives and other appropriate components.

The subject of the present invention is also supplemented foodstuffs both as animal feed and for human consumption, characterized in that they contain the additive conforming to the invention.

These supplemented foodstuffs conforming to the invention may be provided in any form known in the food sector, in the form of a single foodstuff or in the form of a compound foodstuff, and the like.

Within the framework of animal feed, the forms of feedstuffs used will be those customarily known in breeding: powder, liquid, paste form or granules and the like.

Within the framework of foodstuffs for human consumption, the forms of foodstuffs used are those customarily known: powder, paste, liquid and the like.

In addition to the preceding arrangements, the invention also comprises other arrangements, which will emerge from the following description, which refer to examples for implementing the process which is the subject of the present invention.

It should be clearly understood, however, that these examples are given solely by way of illustration of the subject of the invention and do not constitute in any manner a limitation thereof.

EXAMPLE 1: Morphological and Biochemical Characteristics of the Sporolactobacillus P44 Strain According to the Invention.

The Sporolactobacillus P44 strain has the phenotypic traits of the Sporolactobacillus genus; it has, in addition, certain genomic characteristics specific to its species.

The morphological characteristics of this strain are the following:

straight or slightly curved bacilli, fairly thin, with round ends, 3 to 5 μm wide and 0.7–0.8 μm in diameter; they exist in the form of isolated bacilli or in pairs, rarely in the form of short chains; positive motility by peritrichous ciliation; central deforming spores.

The biochemical characteristics are the following:

Gram +, microaerophile to facultative anaerob;

optimal temperature for growth: 30° to 37° C.;

homofermenter;

absence of catalase and cytochromes;

end of culture pH on MRS broth (after incubation for 48 hours under microaerophilic conditions at 37° C.): about 4.30;

under these same conditions, high production of lactic acid:
D-lactic acid: about 54%,
L-lactic acid: about 46%, under different conditions (culture on MRS broth inoculated at 5% and incubated for 24 hours at 37° C. under aerobic conditions), there is production:
of volatile fatty acids (99.9% of $C_2$ and trace amounts of $C_4$),
and lactic acid:
D isomer: 97.5%
L isomer: 2.5%.

The results of an API 50 CHL gallery giving the profile for the fermentation of sugars are presented in FIG. 1; the strain is inoculated according to the API 50 CHL specifications with a suspension of an optical density of about 0.5 to 0.75 measured at 550 nm, that is to say at tube 5 on the MacFarland scale.

EXAMPLE 2: Comparative Restriction Profiles for Sporolactobacillus P44 and *Sporolactobacillus inulinus*.

a) Procedure:

The methodology used is that described by GRIMONT (Annales Institut Pasteur Microbilogie, 1986, 137 B, 165–175) and comprises the following steps:

lysis of the bacteria and extraction of the chromosomal DNA, denaturation of the DNA by phenol and chloroform treatment and purification by ethanol precipitation, cleavage of the DNA with 25 restriction endonucleases and separation of the fragments obtained by electrophoresis on agarose, Southern blotting of the DNA fragments obtained onto a nylon membrane (modified Southern blotting using alkaline blotting under vacuum), hybridization of the fragments with the 16 and 23 S rRNA of *Escherichia coli*, labelled at the 5' end with radioactive phosphorus, washing and visualization by autoradiography of the DNA fragments carrying the genes encoding the ribosomal RNA ribonucleic acids (rRNA).

b) Profile for Sporolactobacillus P44:

12 endonucleases were capable of cleaving the DNA of this strain: BglII, ClaI, SmaI, XbaI, BglI, PvuII, EcoRI, HindIII, EcoRV, XhoI, PstI, MluI; Table I below gives the molecular weights of the restriction fragments of DNA from Sporolactobacillus P44 which hybridize with the 16+23 S RNA of *Escherichia coli*.

TABLE I

BglII: 20.4 - 14.9 - 8.7 - 7.2.
ClaI: 9.5 - 9.3 - 7.6 - 6.8 - 6.4 - 4.2 - 3.2 - 2.6.
SmaI: 20.4- (16.7) - (14.9) - 13.5-10.5- (8.3) - 7.6 - 5.9 - 4.0.
XbaI: 20.4 - 19.8 - 18.5 - 10.5 - 8.3 - 6.8 - (4.5) - (2.0).
BglI: (20.4) - 18.5 - (16.7) - 12.6 - 10.7 - 6.8.
PvuII: 14.9 - 12.5 - 10.6 - 8.4 - 7.5 - 6.5 - (3.2).
EcoRI: 14.4 - 10.6 - 5.8 - 5.3 - 3.5 - 2.7 - 2.5.
HindIII: 17.0 - 7.9 - 7.4 - 7.0 - 5.3 - 3.8 - 3.7 - 3.5 - (3.3) - (3.2) - (2.9) - 1.8.
EcoRV: (17.0) - 13.2 - 12.0 - 8.1 - 6.3 - 5.3 - (3.5).
XhoI: 22.8 - 20.6 - 8.5 - 8.1.
PstI: 13.2 - 8.5 - 7.8 - 7.3 - 7.0 - 6.6 - (4.1) - (3.2) - (2.5).
MluI: (20.6) - 17.0 - 9.5 - 8.1 - 7.0 - 5.8.

c) Profile for *Sporolactobacillus inulinus*:

Under the same conditions as those set out in a) and b) above, the profile illustrated in Table II below is obtained for *Sporolactobacillus inulinus*:

TABLE II

BglII: 14.9 - 13.5 - 10.6 - 9.4 - 8.7 - 6.8.
ClaI: 16.7 - 13.5 - 12.5 - (9.3) - 8.3 - 7.2
SmaI: 20.4 - 16.7 - 12.5 - (11.6) - 8.7 - 6.5 - 3.2 - 2.0.
XbaI: 20.4 - (18.5) -8.3- 7.2- (4.5).
BglI: (20.4) - 18.5 - 12.5 - 10.5 - 7.2.
PvuII: 13.5-10.4- 9.7- 7.6- (4.5) - (3.2).
EcoRI: 22.8 - 20.6 - 17.0 - 14.4 - 12.0 - 9.5 - 8.5 - 4.8- (2.5).
HindIII: 17.0 - 9.5 - 9.0 - 6.2 - 4.1 - 3.8 - 3.7 - 3.5 - 3.2 - (1.8).
EcoRV: 13.2 - 10.6 - 7.9 - 6.3 - 6.2 - (5.3) - (3.5).
XhoI: 22.8 - 20.6 - 14.4 - 12.0 - 8.1.
PstI: 8.5 - 7.4 - 5.8 - (4.1) - (3.2) - (2.5).
MluI: 22.8 - 17.0 - 14.4 - 8.1 - 7.0.

In these two tables, the faint bands, which require an overexposure of the films in order to be observable, are specified in brackets.

d) Comparative Study of the Results Illustrated in Tables I and II:

The profiles illustrated in Tables I and II show that these two strains are clearly different.

EXAMPLE 3: Bioregulatory Effect of Sporolactobacillus P44 on the Assimilation of Lactose According to the Invention Compared with a Control Batch and with a *Clostridium butyricum* 1002.5 Strain, on Male Rats of Fisher 344 breed.

The trials are performed on three lots of gnotobiotic rats bred in sterile experimental isolating devices according to an experimental device described by LECOZ et al. (Sci. Techn. Anim. Lab., (1989), 14., (1), p. 35–39).

The feed with which the animals are fed are sterilized; they are semisynthetic diets suitable for rats, based on maize starch and fish meal from which a fraction of the starch fraction has been replaced either with 8% lactose (Merck) (8% lactose diet), or with 2% lactulose (Duphalac, Duphar) (2% lactulose diet).

These three lots are in conformity with the following description:

1. Axenic rats (control lot).

2. Rats in the monoxenic state (with supply of only one microbial strain in the feed):

either with the *Clostridium butyricum* 1002.5 strain described in POPOFF et al. (Infection and Immunity (1985), 47, p. 697–776).

The rats are kept thirsty overnight and receive the next morning as drinking water, 5 ml of a LAPTTWISS culture broth (10 g of DIFCO yeast autolysate, 15 g of Evans peptone, 10 g of DIFCO tryptone, 1 g of Tween 80, 1 l of distilled water, pH=6.5), of 24 hours ($10^8$ *C. butyricum*/ml), diluted in about 20 ml of distilled water.

After consumption of "this solution", the rats further receive distilled water as drink.

or with Sporolactobacillus P44: according to the needs, the bacterial suspension ($10^7$ microorganisms/ml) is one fourth diluted in sterile distilled water and poured into the feeding bottles. It being necessary for the strain to be given continuously, a new aliquot is introduced into the isolating device every 48 hours.

3. Rats in the dixenic state (with continuous supply of Sporolactobacillus P44 to monoxenic rats after implantation of *Clostridium butyricum* 1002.5 in the intestine):

The *C. butyricum* 1002.5-monoxenized rats continuously receive Sporolactobacillus P44 in their drinking water, as described above.

Rat was chosen because it has an endogenous intestinal enzyme content similar to that of young mammals.

*Clostridium butyricum* 1002.5:

This strain produces:

VFAs: much more butyrate (63%) than acetate (37%), lactic acid: small quantity, gases (hydrogen).

This strain possesses a β-galactosidase inducible with lactose, whose activity is maximum at 40° C. (pH=7).

These characteristics are summarized in Table III below:

TABLE III

| Bacteria | | Sporulating bacillus P44 | *C. butyricum* (BOUSSEBOUA, 1989) | |
|---|---|---|---|---|
| Fermentive metabolites | | Appropriate medium for growing of P44: MRS medium | Appropriate medium for growing of *C. butyricum*: glucose | Appropriate medium for growing of *C. butyricum*: lactose |
| | $Concentration_{Total}$ | 101.2 | 34.1 | 36 |
| Volatile Fatty Acids (mmol/l) | acetate or acetic acid | 101 mmol/l | 12.6 mmol/l | 13.3 mmol/l |
| | (%) | (100%) | (37%) | (36.9%) |
| | butyrate or butyric acid | 0.2 mmol/l | 21.5 mmol/l | 22.7 mmol/l |
| | (%) | (0.2%) | (63%) | (63.1%) |
| | $Concentration_{Total}$ | 113.4 | | 1.2 |
| Lactic acid | D lactic acid (mmol/l) (%) | 110.6 mmol/l (97.5%) | too low to be measured | too low to be measured |
| | L lactic acid (mmol/l) (%) | 2.8 mmol/l (2.5%) | too low to be measured | too low to be measured |
| Gas (hydrogen) | | − | + | + |
| β-galactosidase | | − | + | |

The following metabolic parameters were measured on these different lots:

- characteristics of the assimilation of the lactose and/or the lactulose ingested,
- measurement of the hydrogen excreted,
- lactose/lactulose balance: determination of the quantity of lactose or lactulose ingested and excreted daily so as to deduce therefrom the quantity of sugar metabolized by the animal, thereby making it possible to calculate the CDU (coefficient of digestive use) of each of these sugars.

$$CDU = \frac{\text{quantity of sugar ingested} - \text{quantity of sugar excreted} \times 100}{\text{quantity of sugar ingested}}$$

- Assay of the specific activities of β-galactosidase in the faeces and of the endogenous neutral lactase of the intestinal mucous membrane.

Fermentative characteristics of the 2 strains used:

Sporolactobacillus P44:

The fermentation products present in the MRS culture medium under the conditions of Example 1 are:

- volatile fatty acids: acetate 99.8% and butyrate (trace amounts),
- lactic acid: higher quantity of the D isomer (97.5%) than the L isomer (2.5%).

This strain does not have constitutive or inducible β-galactosidase.

RESULTS:

In the 8% lactose and 2% lactulose diets, the fermentation of lactose like that of lactulose results in the production of hydrogen in rats monoxenic with respect to *Clostridium butyricum* 1002.5.

When the Sporolactobacillus P44 strain is continuously supplied to these rats, a decrease in the production of gas is observed only in rats receiving the 8% lactose diet, this decrease being due to a smaller quantity of sugar fermented by *Clostridium butyricum* 1002.5.

The axenic and monoxenic rats with the Sporolactobacillus P44 strain, which ingest the same quantity of lactose, excrete it in different proportions: the CDU for the lactose of monoxenic rats which is equal to (95.2±0.4) is significantly higher than the CDU of axenic rats (91.7±0.6), which indicates that the quantity of lactose metabolized in the monoxenic animals with this strain, is enhanced by 3.5%.

Furthermore, the dixenic rats totally degrade the lactose and the lactulose (CDU=100%), because of their fermentation in the large intestine by *Clostridium butyricum* 1002.5.

The results of the measurement of the specific activity of the lactase at different levels of the intestine indicate that the continuous supply of the Sporolactobacillus P44 strain induces in monoxenic rats an increase in the duodenal lactase specific activity.

These results clearly show the bioregulatory role of the Sporolactobacillus P44 strain in the assimilation of lactose and therefore the full importance of the use of this strain in lactose-rich dairy products intended for populations more particularly deficient in lactase.

In addition, because of the possibility of having the strain in the form of natural spores, this strain can be used in foodstuffs requiring substantial thermal and/or mechanical treatments while retaining its bioregulatory properties.

As evident from the above, the invention is not in the least limited to the implementations, embodiments and applications which have just been described more explicitly; on the contrary, it embraces all the variants which may occur to a specialist in this field without departing from the framework or the scope of the present invention.

We claim:

1. An isolated strain of Sporolactobacillus having Collection Nationale de Culture de Microorganisms of Institute Pasteur Deposit No. I-1089.

2. Microbial food additive for human consumption or as animal feed, comprising at least one isolated strain of Sporolactobacillus selected from the group consisting of *Sporolactobacillus inulinus* and Sporolactobacillus P44.

3. Microbial food additive consisting essentially of the Sporolactobacillus strain according to claim 1.

4. Microbial food additive consisting essentially of an association of Sporolactobacillus P44 and *Sporolactobacillus inulinus*, acting in symbiosis.

5. Microbial food additive according to claim 2 additionally including ingredients selected from the group consisting of carriers, diluents and preservatives.

6. Supplemented foodstuffs both as animal feed and for human consumption, said foodstuffs containing the additive according to claim 2.

* * * * *